United States Patent [19]

Dori

[11] Patent Number: 5,756,491

[45] Date of Patent: May 26, 1998

[54] ANTIVIRAL COBALT-ORGANIC COMPOUNDS

[75] Inventor: Zvi Dori, Haifa, Israel

[73] Assignee: Chai-Tech Corporation, Greenvale, N.Y.

[21] Appl. No.: 803,259

[22] Filed: Dec. 5, 1991

Related U.S. Application Data

[63] Continuation-in-part of Ser. No. 606,070, Oct. 30, 1990, Pat. No. 5,142,076, which is a continuation of Ser. No. 279,417, Dec. 2, 1988, Pat. No. 5,049,557, which is a continuation-in-part of Ser. No. 147,713, Jan. 25, 1988, Pat. No. 4,866,054, and Ser. No. 147,714, Jan. 25, 1988, Pat. No. 4,866,053, which is a continuation-in-part of Ser. No. 862,804, May 13, 1986, abandoned, said Ser. No. 147,713, is a continuation-in-part of Ser. No. 862,804, May 13, 1986, abandoned.

[51] Int. Cl.⁶ .................... A61K 31/33; C07D 277/60
[52] U.S. Cl. .................... 514/185; 546/6; 548/106
[58] Field of Search .................... 546/6; 548/106; 514/185

[56] References Cited

U.S. PATENT DOCUMENTS 5,049,557  9/1991  Dori et al. .................... 514/183 X

OTHER PUBLICATIONS

Chem. Abstracts; 114:220047h; Varhelgi et al.; Jun. 1991.
Pol. J. Chem., Varhelyi et al. Jun. 1990, pp. 305–316.
Black's Law Dictionary, Revised Fourth Edition, West Publishing Co., St. Paul, MN p. 1159 (1968).
Stedman's Medical Dictionary, 24th Ed. Williams & Wilkins, pp. 1559–1565 (1982).
George J. Galasso, Richard J. Whitley, Thomas C. Meriyan, Ed., *Antiviral Agents and Viral Diseases of Man* Third, Ed., 1990, Raven Press, N.Y.
Russell S. Drago and Barry B. Corden, Acc.Chem.Res. 1980, 13, 353–360 *Spin–Pairing Model of Dioxygen Binding and its Application to Various Transition–Metal Systems* . . . .
Eric C. Niederhoffer, et al, Chem. Rev. 1984, 84, 137 *Thermodynamics of Oxygen Binding in Natural and Synthetic Dioxygen Complexes*.
A.Summerville, et al, J. Chem.Educ., vol. 56, 3, Mar. 1979 *Assigning Oxidation States to Some Metal Dioxygen Complexes of Biological Interest*.
Mary T. Green, Edmund C. Dunkel, Brian L. Morris, Antimicrobial Agents and Chemotherapy, Nov. 1981, pp. 580–582 *Quantitation of Herpes Simplex Virus Type 1 Shed in Preocular Tear Film of Rabbits Treated with Acyclovir*.
Melvin D. Trousdale, Edmund C.Dunkel, and Anthony B. Nesburn, Invest. Opthalmol. Vis.Sci., vol. 19, No. 11, (1980) pp. 1336–1341 *Effect of acyclovir on acute and latent herpes simplex virus infections in the rabbit*.
Melvin D. Trousdale, Edmund C. Dunkel, and Anthony B. Nesburn, Invest. Opthalmol. Vis.Sci., vol. 19, No. 3, (1980) pp.267–270 *Effect of flurbiprofen on herpes simplex keratitis in rabbits*.
Marty T. Green and Edmund C. Dunkel, Invest. Opthalmol Vis.Sci., vol. 21, No. 6, (1981) pp. 882–886 *Quantitation of herpes simplex virus in vitro and in preocular tear film*.
Green, Dunkel, Pavan–Langston, Exp. Eye Res. (1987) 45, pp. 375–387, *Effect of Immunization and Immunosuppression on Induced Ocular Shedding and Recovery of Herpes Simplex*.
Pavan–Langston, Campbell, Lass; Am.J. of Ophthalm. 86:618–623, 1978, *Acyclic Antimetabolite Therapy of Experimental Herpes Simplex Keratitis*.

(List continued on next page.)

*Primary Examiner*—Johann Richter
*Assistant Examiner*—T. A. Solola
*Attorney, Agent, or Firm*—McAulay Fisher Nissen Goldberg & Kiel, LLP

[57] ABSTRACT

Compounds having the formula

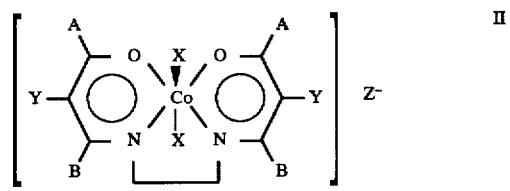

wherein each

A may be the same or different and is an alkyl group, a phenyl group or a substituted derivative of a phenyl group;

Y may be the same or different and is hydrogen, an unbranched alkyl group, a halide or a group having the structure

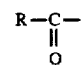

wherein R is hydrogen, an alkoxide group, an alkyl group, or OH;

B may be the same or different and each is hydrogen or an alkyl group;

Z⁻ is a soluble, pharmaceutically acceptable negative ion, and

X may be the same or different and is an axial ligand selected from the group consisting of moieties having the formula:

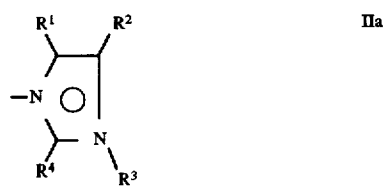

The compounds and compositions thereof exhibit antiviral activity.

19 Claims, No Drawings

OTHER PUBLICATIONS

Sabbaga, Pavan–Langston, Bean, Dunkel, Exp. Eye REs. (1988) 47, pp. 545–553 *Detection of HSV Nucleic Acid Sequences in the Cornea During Acute and Latent Ocular Disease.*

Boisjoly, Woog, Pavan–Langston, Park. Arch Opthalmol vol. 102. Dec. 1984, pp. 1804–1807, *Prophylactic Topical Cyclosporine in Experimental Herpetic Stromal Keratitis.*

Pavan–Langston, Dunkel, Arch Ophthalmol. vol. 107, Jul. 1989, pp. 1068–1072, *Ocular Varicella Zoster Virus Infection in the Guinea Pig.*

Getz, Melamud, Silver, Dori, J.Am. Chem. Soc. 97:13 Jun. 25, 1975, *Electronic Structure of Dioxygen in Cobalt (II) Oxygen Carriers, Singlet Oxygen or $O_2$–?.*

Kern, Antiviral Agents and Viral Diseases of Man, 3rd.Ed., Chapter 3, *Preclinical Evaluation of Antiviral Agents; In Vitro and Animal Model Testing* (1990) Raven Press, NY.

Pavan–Langston, Antiviral Agents and Viral Diseases of Man, 3rd, Ed. Chapter 6, *Major Ocular Viral Infections,* (1990) Raven Press, N.Y.

ANTIVIRAL COBALT-ORGANIC COMPOUNDS

CROSS-REFERENCE TO RELATED APPLICATIONS

The present application is a continuation-in-part of U.S. application Ser. No. 07/606,070, filed Oct. 30, 1990, now U.S. Pat. No. 5,142,076 which in turn is a continuations of U.S. application Ser. No. 07/279,417, filed on Dec. 2, 1988, now U.S. Pat. No. 5,049,557 which, in turn, is a continuation-in-part of U.S. application Ser. No. 07/147,713 and U.S. application Ser. No. 07/147,714, both filed on Jan. 25, 1988, now U.S. Pat. Nos. 4,866,054 and 4,866,053, respectively, which, in turn, are continuation-in-parts of U.S. application Ser. No. 06/862,804, filed on May 13, 1986, now abandoned. The contents of U.S. application Ser. No. 502, 294, now U.S. Pat. No. 5,106,841 and Ser. No. 06/862,804 and U.S. Pat. Nos. 5,049,557, 4,866,054, 5,142,076 and 4,866,053 are hereby incorporated by reference into the present disclosure.

BACKGROUND OF THE INVENTION

The present invention relates to metallo-organic cobalt compounds and their use in the treatment of subjects for conditions and diseases caused by viruses and viral infections. It has been discovered that certain conditions and diseases, e.g., inflammation, burns, wounds, and diseases caused by bacteria and fungi in mammalian species can be treated with certain complexes of cobalt having the structure:

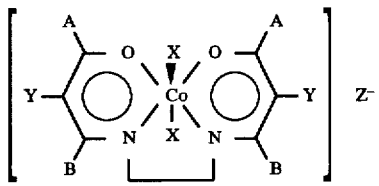

wherein each A may be the same or different and is an alkyl group, a phenyl group or a substituted derivative of a phenyl group;

wherein each Y may be the same or different and is hydrogen, an unbranched alkyl group, a halide or a group having the structure

wherein R is hydrogen, an alkoxide group, an alkyl group, or OH;

wherein each B may be the same or different and each is hydrogen or an alkyl group;

wherein each X may be the same or different and each is a water soluble group having weak to intermediate ligand field strength; and $Z^-$ is a soluble, pharmaceutically acceptable negative ion.

Today, virus infections are known to be significant causes of morbidity and mortality in human and veterinary medicine. Many of these diseases are untreatable or the available therapies are not entirely satisfactory and only provide minimal clinical response. For the most part, it is known that viral diseases do not respond to therapy with conventional antibiotics. Despite some recent successes in the development of antiviral chemical therapeutic agents, new treatments for these diseases are needed to improve the management of viral infections in clinical medicine.

Parent application Ser. No. 606,070, now U.S. Pat. No. 5,142,076, referred to herein above, discloses the use of the foregoing described compounds as antiviral agents.

SUMMARY OF THE INVENTION

I have now discovered a series of new compounds having the structure:

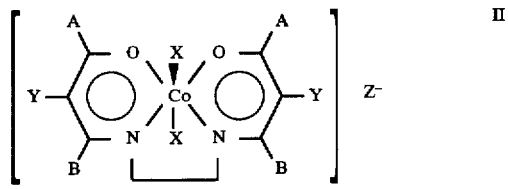

wherein each A may be the same or different and is an alkyl group, a phenyl group or a substituted derivative of a phenyl group;

each Y may be the same or different and is hydrogen, an unbranched alkyl group, a halide or a group having the structure

wherein R is hydrogen, an alkoxide group, an alkyl group, or OH;

each B may be the same or different and each is hydrogen or an alkyl group;

$Z^-$ is a soluble, pharmaceutically acceptable negative ion, and each X may be the same or different and is an axial ligand selected from the group consisting of moieties having the formula:

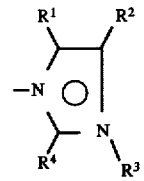

wherein $R^1$, $R^2$, $R^3$, and $R^4$ may be the same or different and may be hydrogen or lower alkyl having from 1 to 4 carbon atoms; and

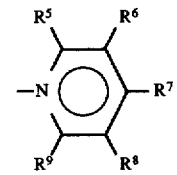

wherein $R^5$, $R^6$, $R^7$, $R^8$ and $R^9$ may be the same or different and may be selected from the group consisting of electron donating groups and electron withdrawing groups, with the proviso that $R^1$, $R^2$, $R^3$, $R^4$, $R^5$, $R^6$, $R^7$, $R^8$, and $R^9$ are of a sufficiently small size so as not to prohibit the attachment of the axial ligand to the Co atom due to steric hindrance.

As used herein, the term "axial" when used in conjunction with the term "ligand" refers to the fact that the ligand is oriented outside the plane of the molecule and has the same meaning as described in connection with FIG. 1 of U.S. Pat. No. 5,049,557. As used herein, and unless otherwise indicated, an alkyl group means a linear, branched or cyclic alkyl group containing from one to six carbon atoms.

The inventive compounds having the structure of Formula II exhibit significant activity as antiviral agents and can be used for treating viral infections as is, or in a composition form when combined with a pharmaceutically acceptable carrier. Depending on the nature of the infection and the manner in which it manifests itself, the inventive antiviral compositions may be administered by using conventional modes of administration, e.g., oral, topical application, parenteral, and the like.

The antiviral composition of the invention comprises a suitable pharmaceutically acceptable carrier and the inventive compound in an amount effective to suppress the replication and/or abort the infective life cycle of the virus causing the infection.

BRIEF DESCRIPTION OF THE DRAWINGS

FIGS. 1 through 7 are graphs depicting stromal disease studies in animals treated with the inventive compounds and comparison compounds.

DETAILED DESCRIPTION OF THE INVENTION

The compounds of the present invention may be crystallized with numerous counteranions. Counter-anions which are pharmaceutically acceptable and are water soluble, such as, halide ions, $PF_6^-$ and $BF_4^-$, are preferred. The bromide and chloride salts of the present compounds are the most preferred because they are more water soluble than other salts of the compounds.

As discussed above, A may be an alkyl group, a phenyl group or a substituted derivative of a phenyl group. Preferably, the alkyl group is a $C_1$–$C_5$ group with methyl, ethyl, and butyl groups being particularly preferred. Suitable substituted derivatives of the phenyl group are derivatives wherein each substituent is a halide, an alkyl group or a group having the structure

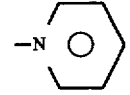

where R is hydrogen, an alkoxide group, an alkyl group or an OH group. To date, the most useful derivatives have proven to be those in which the substituents are halides, or alkyl groups.

Y may be hydrogen, an unbranched alkyl group, a halide or a group having the structure

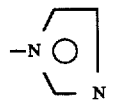

where R is hydrogen, an alkoxide group, an alkyl group, or an OH group. In certain embodiments, it is preferred that Y is chlorine, hydrogen atom or a $C_1$–$C_3$ alkyl group. In embodiments where Y has a structure

it is preferred that R is hydrogen, a methyl group, or an OH group.

B may be hydrogen or an alkyl group, and preferably is a $C_1$–$C_3$ alkyl group.

X may be imidazole or pyridinyl groups linked to the cobalt atom through a nitrogen of the ring. The imidazole or pyridinyl nuclei may have hydrogen atoms, or electron donating or withdrawing groups substituted thereon.

The electron withdrawing or donating groups which may constitute appendant groups $R^1$, $R^2$, $R^3$, $R^4$, $R^5$, $R^6$, $R^7$ and $R^8$ are those known in the art to exert the specified electron withdrawing or donating effects on aromatic nuclei. Typical of electron donating groups are alkyl, hydroxyl, and the like. Typical of electron withdrawing groups are $NO_2^-$, $Cl^-$, $Br^-$, and the like. The identity of the particular group is not crucial so long as it does not impart properties to the molecule which are detrimental to the desired properties of the compound, e.g., decreased antiviral activity, increased toxicity, and the like. Additionally, the group must not be so large as to prevent the axial ligand to attach to the cobalt atom due to steric effects, e.g., steric hindrance.

Preferably, the groups attached to the imidazole nucleus are alkyl having from one to three carbon atoms. Of these, methyl and ethyl are most preferred. Preferred are the unsubstituted, 2-methyl, 4-methyl, and 2-ethyl imidazoles and the unsubstituted pyridinyl.

The following Table provides the structures of preferred compounds in accordance with the present invention. Compound 23, disclosed in the parent application Ser. No. 606,070 as exhibiting antiviral activity, is included as it is provided as a comparison in the examples that follow. In the following diagram, B is, in each case, methyl, and A, Y, X and $Z^-$ refer to those symbols as used in Structure II.

| COMPOUND | Y | X | Z | A |
| --- | --- | --- | --- | --- |
| 23 | H | $-NH_3$ | Cl | $-CH_3$ |
| 76 | H |  | Br | $-CH_3$ |
| 82 | H | 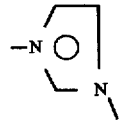 | Cl | $CH_3$ |
| 93 | Cl | 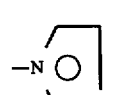 | Br | $-CH_3$ |
| 96 | H |  | Br | $-CH_3$ |

-continued

| COMPOUND | Y | X | Z | A |
|---|---|---|---|---|
| 97 | H | 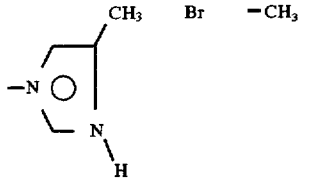 | Br | —CH₃ |
| 98 | H | 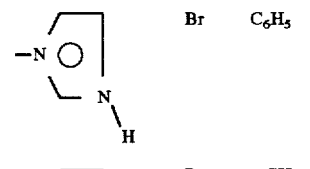 | Br | C₆H₅ |
| 100 | Cl | 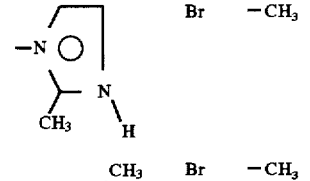 | Br | —CH₃ |
| 101 | Cl | 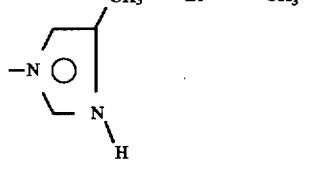 | Br | —CH₃ |
| 102 | H | 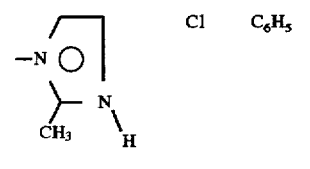 | Cl | C₆H₅ |
| 109 | H | 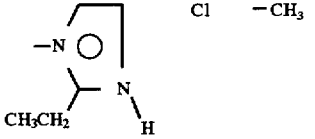 | Cl | —CH₃ |

The inventive composition comprises a pharmaceutically acceptable carrier and the compound as defined above in an antiviral effective amount. It is understood, of course, that generally in the treatment of conditions which result from viral infections, a regimen of treatment is required in which the medication is provided in periodic dosages over a period of time.

In any event, in treatments using the inventive compounds, it is important that an antiviral effective amount or dosage and an antiviral effective dosage regimen be used. As used herein, the expression antiviral effective amount or dosage or regimen means that amount, dosage or regimen which results in sufficient concentrations of the particular compound at the cellular sites of infection which are sufficiently in excess of those concentrations necessary to inhibit virus replication and/or abort the virus's effective life cycle.

The inventive compounds and compositions may be used in treating infections caused by a variety of viruses. Certain compounds within the group may exhibit greater efficacy against specified viruses as compared with other compounds within the inventive group. Accordingly, the present invention includes the inventive compositions wherein the composition contains a compound as defined herein above in an amount which is effective against the specific virus being treated. Known viruses of clinical significance are disclosed in Stedman's Medical Dictionary, 24th Ed., Williams & Wilkins, pp. 1559–1565, (1982); Virology, B. N. Fields, D. M. Knipe, R. M. Chanock, J. L. Melnick, & R. E. Shope, Raven Press, N.Y. (1985). See also Antiviral Agents and Viral Diseases of Man, George J. Galasso, Richard J. Whitley, and Thomas C. Meriyan, Ed., Third Edition, 1990, Raven Press, N.Y.

The inventive compounds are particularly effective against, inter alia, herpes virus, e.g., HSV-1, HSV-2, CMV, VZV, HHV-6, EBV and the like.

The inventive composition may be administered orally, in suitable dosage forms, for example, dragees, capsules, tablets, elixirs, or other oral dosage forms. Also, the composition can be administered subcutaneously, e.g., in sterile distilled water or physiological saline. For topical administration, the inventive composition may be placed in dimethyl sulfoxide (DMSO), physiological saline or in the form of ointments, salves, creams, and the like.

Typically, the dosage may be administered 1 to 9 times daily, depending upon the severity and nature of the viral condition or on a schedule less frequent than daily, e.g., every other day, weekly, and the like. The inventive compound may be formulated in a sustained release or controlled release compositions such as that consisting of a microencapsulated form, or through other systems such as encapsulation within liposomes. These sustained release systems can permit less frequent dosing while achieving the desired therapeutic efficacy. Preferably, the administration is under medical supervision so that the dosage may be reduced or the number of daily administrations limited as the viral infection subsides.

The compounds of the present invention are water soluble, although the degree of solubility may vary from compound to compound, and may be dissolved in a number of conventional pharmaceutically acceptable carriers. Suitable carriers include polar, protic solvents, such as, water, or normal saline. The compounds may also be suspended in a suspension medium that is not miscible with water, for example, petrolatum.

When these inventive compositions are to be administered by the topical route, the concentration in the solvent suspension medium can vary from 0.1 to 50 mg/ml. A preferred concentration range lies between 0.5 and 10 mg/ml.

When the inventive compositions are to be given or parenteral routes, a dosage range of 0.01 mg/kg body weight/day to 100 mg/kg body weight/day can be used.

General methods for the synthesis of the compounds of the present invention are described in U.S. Pat. No. 5,049,557 referred to and incorporated by reference herein-above. As noted therein, the reaction of Co(II) complexes with molecular oxygen has been studied extensively (see, R. S. Drago and B. R. Corden, Acc. Chem. Res., 1980, 13, 353 & E. C. Niederhoffer, J. H. Timmons and A. E. Martell, Chem. Rev. 1984, 84, 137). Normally, cobalt (II) forms 2:1 peroxo bridged complexes in aqueous solutions (see, E. C. Niederhoffer, J. H. Timmons and A. E. Martell, Chem. Rev. 1984, 84, 137). In recent years, a number of Co(II) complexes have been reported to give 1:1 cobalt-oxygen adducts at room temperature. These complexes usually contain ligands which when bound to Co(II) give rise to a low spin planar geometry. Addition of base and O₂ to these complexes leads to the formation of octahedral complexes where the base and the O₂ occupy axial positions (see, A. Summerville, R. D. Jones, B. M. Hoffman and F. Basolo, J. Chem. Educ., 1979, 56, 3, 157).

On the basis of measurements utilizing a variety of physical techniques, it is now a well-accepted fact that the most accurate electronic structure description of the Co:O₂ moiety is a Co(III) ion bound to $O_2^-$, where the actual amount of Co→$O_2$ electron transfer depends on the nature of the ligand and the donor set (see, A. Summerville, R. D. Jones, B. M. Hoffman and F. Basolo, J. Chem. Educ., 1979, 56, 3, 157, & D. Getz, E. Melamud, B. L. Silver and Z. Dori, J. Am. Chem. Soc., 1975, 97, 3846). It has been shown that electron transfer increases with increase of the ligand field strength (see, R. S. Drago and B. R. Corden, Acc. Chem. Res., 1980, 13, 353). This can be easily understood from the molecular orbital diagram depicted in FIG. 1 of U.S. Pat. No. 5,049,557 and the description therein.

The following examples illustrate the present invention. The methods used in the examples are described in the following references:

1. For in vitro titer determination in a modified Vero cell culture model and in tear film (Example 3), see Green and Dunkel, Antimicrob Agents and Chemother 20; 580–582, 1981; and Green and Dunkel, Invest. Ophthalmol. Vis. Sci. 19; 1336–1341, 1981.

2. For in vivo epithelial HSV-1 induced keratitis (Example 3, 4 and 5), see Trousdale, Dunkel, Nesburn, Invest. Ophthalmol. Vis. Sci. 19; 267–270, 1980; Pavan-Langston, Lass, Campbell, Am. J. Ophthalmol. 86; 618–623, 1978; Green, Dunkel, Pavan-Langston, Exp. Eye Res. 45; 375–387, 1987.

3. For in vivo stromal HSV-1 induced keratitis, see Sabbaga, Pavan-Langston, Bean, Dunkel, Exp. Eye Res. 47; 545–553; Boisjoly, Woog, Pavan-Langston, Park, Arch. Ophthalmol. 102; 1804–1807, 1984; Pavan-Langston, Dunkel, Arch. Ophthalmol. 107; 1068–1072, 1989.

4. For in vitro activity and toxicity of antiviral drugs for herpes viruses, see also, *Antiviral Agents and Viral Diseases of Man*, supra. In particular, Chapter 3, Preclinical Evaluation of Antiviral Agents: *In vitro and Animal Model Testing* by Dr. Earl R. Kern; and Chapter 6, *Major Ocular Viral Infections* by Dr. Deborah Paran-Langston.

EXAMPLE 1

In vitro Assays With HSV-1 Virus

In vitro assays were carried out to determine the direct virucidal efficacy of the compound to be tested, the potential toxicity of the compound and the intracellular anti-viral activity. The tests were carried out as follows:

A. Viral Strain Used

HSV-1 McKrae Strain was diluted to a final concentration of $10^5$ PFU/ml in minimal essential medium (MEM). Hereinafter, this dilution is referred to as the HSV-1 Suspension for convenience.

B. Preparation of Solutions of Inventive Compound to be Tested

A stock solution of each compound to be tested at a concentration of 5 mg/ml was prepared. The stock solution was serially diluted in Hank's Balanced Salt Solution (HBSS) to obtain final drug concentrations of 5, 2, 1, 0.5, 0.1, 0.01, 0.001 and 0.0001 mg/ml. At the time of these experiments, certain of the compounds were observed to be insoluble at the higher concentrations. In such cases, the highest dissolved concentration that could be obtained was utilized. It was subsequently found that the insolubility was due solely to the technique used for solubilization, i.e., insufficient stirring was used. With sufficient stirring, all the compounds completely dissolved.

C. Determination of Direct Virucidal Efficacy

Each of the drug solutions were mixed with the HSV-1 Suspension in a 1:1 ratio. The drug and HSV-1 Suspension mixture was incubated at 37° C. for thirty minutes with agitation every ten minutes. After the incubation, fifty microliter aliquots were overlaid onto triplicate confluent human foreskin fibroblast (HFF) cell monolayers. The inoculum was absorbed for thirty minutes and then a medium containing the appropriate drug concentration in MEM was added to the monolayers to a final volume of 0.5 milliliters per culture-well. The monolayers were incubated at 37° C. The developing HSV-1 Cytopathology was monitored daily for two days by inverted light microscopy. Titers were calculated by multiple regression analysis. All data is presented as the average PFU/ml reduction at 24 and/or 48 hours after inoculation (PI).

D. Controls

Sham-inoculated, non-treated HFF Cell monolayers were included along with the drug-treated monolayers as "cell monolayer controls".

1. HSV-1 inoculated, non-compound treated HFF monolayers were included as "positive controls"; and 2. Sham-inoculated compound treated HFF monolayers were included to demonstrate potential "toxicity effects" of the compounds.

E. Determination of Intracellular Antiviral Activity

HFF cell monolayers were inoculated with the HSV-Suspension prepared as above by absorption for thirty minutes at 37° C. After absorption of the virus, the inoculum was aspirated from the cell monolayers and the HSV-1 infected monolayers were rehydrated with medium containing the appropriate concentration of the solution of the compound by adding 500 microliters of each compound concentration to triplicate HSV-1 infected monolayers. All monolayers were incubated at 37° C. The developing HSV-1 cytopathology was monitored daily for two days by inverted light microscopy and titers were calculated by multiple progression analysis. For the intracellular anti-viral activity, "cell monolayer controls" were obtained using sham inoculated non-treated HFF cell monolayers along with the drug treated monolayers. "Positive controls" were obtained by using HSV-1 inoculated non-CTC compound treated HFF monolayers.

F. Results

In the tables, the symbols have the meaning indicated:

+=toxic;

−=no toxicity;

±=mild toxicity;

ND=not done;

T=toxicity effects interfered with CPE rating;

CPE=cytopathic effect.

EXPERIMENT 1

RESULTS

Cell monolayer controls

No adverse HFF cellular effects were evident in these monolayers.

TABLE 1

TOXICITY EFFECTS CONTROLS

| COMPOUND | TIME (PI) | Concentration (mg/ml) | | | | |
|---|---|---|---|---|---|---|
| | | 10 | 1 | 0.1 | 0.01 | 0.001 |
| UNTREATED | 24 | − | − | − | − | − |
| | 48 | − | − | − | − | − |
| 23 | 24 | +/− | − | − | − | − |
| | 48 | + | +/− | − | − | − |
| 82 | 24 | − | − | − | − | − |
| | 48 | +/− | − | − | − | − |

TABLE 1-continued

TOXICITY EFFECTS CONTROLS

| COMPOUND | TIME (PI) | Concentration (mg/ml) | | | | |
|---|---|---|---|---|---|---|
| | | 10 | 1 | 0.1 | 0.01 | 0.001 |
| 76 | 24 | +/− | +/− | − | − | − |
| | 48 | + | + | − | − | − |

TABLE 2

VIRUCIDAL EFFICACY

| Compound | Time (PI) | Concentration (mg/ml) | | | | | |
|---|---|---|---|---|---|---|---|
| | | 0 | 10 | 1 | 0.1 | .01 | 0.001 |
| UNTREATED | 24 | $10^6$ | — | — | — | — | — |
| | 48 | $10^7$ | | | | | |
| 23 | 24 | ND | 0 | 0 | $10^1$ | $10^3$ | $10^5$ |
| | 48 | ND | O/T | $10^5$ | $10^5$ | $10^{5-6}$ | $10^{5-6}$ |
| 82 | 24 | ND | 0 | $10^{1-2}$ | $10^2$ | $10^4$ | $10^5$ |
| | 48 | ND | O/T | $10^5$ | $10^{5-6}$ | $10^{5-6}$ | $10^{5-6}$ |
| 76 | 24 | ND | T | T | $10^{1-2}$ | $10^3$ | $10^5$ |
| | 48 | ND | T | T | $10^{5-6}$ | $10^{5-6}$ | $10^{5-6}$ |

TABLE 3

EFFECTIVE VIRUCIDAL CONCENTRATION

| Compound | $IC_{50}$ | $IC_{90}$ |
|---|---|---|
| 23 | 0.01 mg/ml | 0.1 mg/ml |
| 82 | 0.1 mg/ml | 1 mg/ml |
| 76 | 0.01 mg/ml | 0.1–1 mg/ml |

Comment:
The toxicity of compound of 82 was determined to be one order of magnitude less than the observed toxicity of 23 and 76. The virucidal efficacy of 82 ($IC_{50}$) was one order of magnitude less than that observed for 23 and 76. Thus for these compounds, it appears that a reduction in HFF cell toxicity was exchanged for virucidal efficacy.

EXPERIMENT 2

RESULTS

Cell monolayer controls

No adverse HFF cellular effects were evident in these monolayers.

TABLE 4

TOXICITY EFFECTS CONTROLS

| Compound | Time | Concentration (mg/ml) | | | | |
|---|---|---|---|---|---|---|
| | | 10 | 1 | 0.1 | 0.01 | 0.001 |
| Non-treated | 24 | — | — | — | — | — |
| | 48 | — | — | — | — | — |
| 96-Br | 24 | Insol. | — | — | — | — |
| | 48 | Insol. | — | — | — | — |

TABLE 5

VIRUCIDAL EFFICACY

| Therapy | Time (PI) | Concentration (PFU mg/ml) | | | | | |
|---|---|---|---|---|---|---|---|
| | | 0 | 10 | 1 | 0.1 | 0.01 | 0.001 |
| UNTREATED | 24 | $10^{6*}$ | | | | | |
| | 48 | $10^7$ | | | | | |
| 23 | 24 | ND | 0 | 0 | $10^1$ | $10^2$ | $10^3$ |
| | 48 | ND | O/T | 0 | $10^5$ | $10^{5-6}$ | $10^{5-6}$ |
| 82 | 24 | ND | 0 | $10^{1-2}$ | $10^2$ | $10^{2-3}$ | $10^4$ |
| | 48 | ND | O/T | $10^5$ | $10^{5-6}$ | $10^{5-6}$ | $10^{5-6}$ |
| 76 | 24 | ND | T | T | $10^{1-2}$ | $10^{2-3}$ | $10^{4-5}$ |
| | 48 | ND | T | T | $10^{5-6}$ | $10^{5-6}$ | $10^{5-6}$ |
| 96 | 24 | ND | Insol | 0 | $10^{2-3}$ | $10^{2-3}$ | $10^4$ |
| | 48 | ND | Insol | 0 | $10^{5-6}$ | $10^6$ | $10^{5-6}$ |

TABLE 6

EFFECTIVE VIRUCIDAL CONCENTRATION

| Compound | $IC_{50}$ | $IC_{90}$ |
|---|---|---|
| 23 | 0.1 mg/ml | 1.0–0.1 mg/ml |
| 82 | 0.1 mg/ml | 1 mg/ml |
| 76 | 0.01 mg/ml | 0.1–1 mg/ml |
| 96 | 0.1 mg/ml | 1.0–0.1 mg/ml |

Comment:
Compound 96 was insoluble at 10 mg/ml. A stock solution at a concentration of 1 mg/ml was moderately insoluble. As noted above, it was later discovered that this insolubility was due to insufficient stirring. However, a lack of toxicity of 96 was evident at 1 mg/ml and the antiviral activity was similar to that observed for 23.

EXPERIMENT 3

RESULTS

Cell monolayer controls

No adverse HFF cellular effects were evident in these monolayers.

TABLE 7

TOXICITY EFFECTS CONTROLS

| COMPOUND | TIME (PI) | Concentration (mg/ml) | | | |
|---|---|---|---|---|---|
| | | 1 | 0.1 | 0.01 | 0.001 |
| UNTREATED | 24 | − | − | − | − |
| | 48 | − | − | − | − |
| 23 | 24 | +/− | − | − | − |
| | 48 | +/− | − | − | − |
| 96 | 24 | − | − | − | − |
| | 48 | − | − | − | − |

TABLE 8

VIRUCIDAL EFFICACY

| Compound | Time (PI) | Concentration (mg/ml) | | | | |
|---|---|---|---|---|---|---|
| | | 0 | 1 | 0.1 | 0.01 | 0.001 |
| UNTREATED | 24 | $10^6$ | | | | |
| | 48 | $10^7$ | | | | |
| 23 | 24 | ND | 0 | $10^1$ | $10^3$ | $10^5$ |
| | 48 | ND | $10^5$ | $10^5$ | $10^{5-6}$ | $10^{5-6}$ |

TABLE 8-continued

VIRUCIDAL EFFICACY

| Compound | Time (PI) | Concentration (mg/ml) | | | |
|---|---|---|---|---|---|
| | | 0 | 1 | 0.1 | 0.01 | 0.001 |
| 96 | 24 | ND | 0 | $10^{1-2}$ | $10^{3-4}$ | $10^5$ |
|    | 48 | ND | $10^5$ | $10^{5-6}$ | $10^{5-6}$ | $10^{6-7}$ |

EXPERIMENT 4

Cell monolayer controls

No adverse HFF cellular effects were evident in these monolayers.

Antiviral Efficacy of the compounds in vitro.

TABLE 9

VIRUCIDAL EFFICACY (24 Hours PI)

| Compound | Concentration (mg/ml) | | | | | |
|---|---|---|---|---|---|---|
| | 5 | 1 | 0.5 | 0.1 | 0.01 | 0.001 |
| | RUN 1 | | | | | |
| 93 | 0 | 0 | $10^2$ | $10^{2-3}$ | $10^{3-4}$ | $10^5$ |
| 96 | 0 | $10^{1-2}$ | $10^{1-2}$ | $10^{1-2}$ | $10^{2-3}$ | $10^{4-5}$ |
| | RUN 2 | | | | | |
| 93 | 0 | 0 | 0 | 0 | $10^2$ | $10^{4-5}$ |
| 96 | 0 | 0 | $10^{1-2}$ | $10^2$ | $10^4$ | $10^{4-5}$ |

Non-treated = $10^{5-6}$

TABLE 10

TOXICITY EFFECTS CONTROLS

| Compound | Time hrs Post Incubation | Concentration (mg/ml) | | | | | |
|---|---|---|---|---|---|---|---|
| | | 5 | 1 | 0.5 | 0.1 | 0.01 | 0.001 |
| Untreated | | no cellular effects | | | | | |
| 93 | 24 | +/− | − | − | +/− | − | − |
|    | 48 | +/− | − | − | +/− | − | − |
| 96 | 24 | +/− | − | − | +/− | − | − |
|    | 48 | +/− | +/− | − | +/− | − | − |

TABLE 11

EFFECTIVE VIRUCIDAL CONCENTRATION

| Compound | $IC_{50}$ | $IC_{90}$ |
|---|---|---|
| 93 | 0.5 mg/ml | >1.0 mg/ml |
| 96 | 0.5–0.1 mg/ml | >1 mg/ml |

Comment:
The intracellular antiviral activity of the compounds is at least one log higher than the virucidal activity. This indicates that the inventive compounds have a direct virucidal effect on the HSV-1 in addition to having an intracellular effect on the HSV-1. The intracellular effect appears to be non-specific and time dependent.

EXPERIMENT 5

RESULTS

TABLE 12

VIRUCIDAL EFFICACY

24 Hour Post Inoculation

| Compound | Concentration (mg/ml) | | | | | |
|---|---|---|---|---|---|---|
| | 5 | 1 | 0.1 | 0.01 | 0.001 | 0.0001 |
| | Run 1 | | | | | |
| 96 | 0 | 0 | $10^2$ | $10^{2-3}$ | $10^{3-4}$ | $10^5$ |
| 97 | 0 | 0 | $10^1$ | $10^4$ | $10^5$ | $10^5$ |
| 102 | 0 | 0 | $10^2$ | $10^{2-3}$ | $10^4$ | $10^{4-5}$ |
| 104 | 0 | 0 | $10^2$ | $10^3$ | $10^{3-4}$ | $10^5$ |
| | Run 2 | | | | | |
| 96 | 0 | 0 | 0 | $10^3$ | $10^3$ | $10^3$ |
| 97 | 0 | 0 | 0 | $10^1$ | $10^4$ | $10^{4-5}$ |
| 102 | 0 | 0 | 0 | $10^2$ | $10^4$ | $10^{4-5}$ |
| 104 | 0 | 0 | 0 | $10^{2-3}$ | $10^{4-5}$ | $10^{4-5}$ |

Non-treated = $10^5$

TABLE 13

TOXICITY EFFECTS CONTROLS

| Compound | Time hrs Post Incubation | Concentration mg/ml | | | | | |
|---|---|---|---|---|---|---|---|
| | | 5 | 1 | 0.5 | 0.1 | 0.01 | 0.00 |
| Untreated | | No cellular effects | | | | | |
| 96 | 24 | +/− | +/− | − | +/− | − | − |
|    | 48 | + | +/− | − | +/− | − | − |
| 97 | 24 | +/− | +/− | − | +/− | − | − |
|    | 48 | + | +/− | − | +/− | − | − |
| 102 | 24 | +/− | +/− | − | − | − | − |
|     | 48 | + | +/− | +/− | − | − | − |
| 104 | 24 | +/− | +/− | − | +/− | − | − |
|     | 48 | +/− | +/− | − | +/− | − | − |

TABLE 14

EFFECTIVE VIRUCIDAL CONCENTRATION

| Compound | $IC_{50}$ | $IC_{90}$ |
|---|---|---|
| 96 | 0.1–1.0 mg/ml | >1 mg/ml |
| 97 | 0.1–.1 mg/ml | 0.1–1 mg/ml |
| 102 | 0.01–.1 mg/ml | >1.0 mg/ml |
| 104 | 0.1 mg/ml | >1.0 mg/ml |

Comment:
The $IC_{50}$ and $IC_{90}$ drug levels are calculated based upon the reduction in HSV titer compared to the non-drug treated control monolayers. As was observed previously, reduction in toxicity resulted in a reduction in efficacy.

EXPERIMENT 6

Cell monolayer controls

No adverse HFF cellular effects were evident in these monolayers.

TABLE 15

TOXICITY EFFECTS CONTROLS 48 hours Post Incubation
Concentration (mg/ml)

| COMPOUND | 5 | 2 | 1 | 0.5 | 0.1 | 0.01 | 0.001 |
|---|---|---|---|---|---|---|---|
| 93 | ND | ND | +/− | ++/− | ++/− | − | − |
| 96 | +/− | +/− | − | ++/− | ++/− | − | − |
| 23 | +/− | +/− | − | − | − | − | − |

TABLE 16

VIRUCIDAL EFFICACY (24 Hours PI)

Concentration (mg/ml)

| Compound | 5 | 2 | 1 | 0.5 | 0.1 | 0.01 | 0.001 |
|---|---|---|---|---|---|---|---|
| 93 | ND | ND | 0 | 0 | $10^2$ | $10^{2-3}$ | $10^{3-5}$ |
| 96 | 0 | 0 | 0 | 0 | $10^{1-2}$ | $10^{2-3}$ | $10^{3-4}$ |
| 23 | 0 | 0 | 0 | 0 | $10^{0-1}$ | $10^{1-2}$ | $10^{3-4}$ |

Non-treated = $10^{4-5}$

TABLE 17

EFFECTIVE VIRUCIDAL CONCENTRATION

| Compound | $IC_{50}$ |
|---|---|
| 93 | 0.1 mg/ml |
| 96 | 0.1 mg/ml |
| 23 | 0.01 mg/ml |

Comment:
The $IC_{50}$ drug level was calculated based upon the reduction in HSV titer compared to the non-drug treated control monolayers. Reduction in toxicity (e.g. 93 and 96) resulted in a reduction in efficacy of the compounds in this virucidal assay. The toxicity observed with 93 and 96 was demonstrated again. The toxicity appears to be more pronounced in the 0.5 and the 0.1 mg/ml concentrations. The toxicity was evident as cell rounding, detaching from the monolayer, increased granularity and loss of normal morphology. At concentrations below the 0.5 and 0.1 mg/ml, the cell monolayers appeared (visually) to be normal with no overt toxic effects.

EXPERIMENT 7

TABLE 18

ANTIVIRAL EFFICACY

24 Hour Post Inoculation Efficacy;
PFU/ml
Concentration (mg/ml)

| Compound | 5 | 2 | 1 | 0.5 | 0.1 | 0.01 | 0.001 |
|---|---|---|---|---|---|---|---|
| 93 | ND | ND | 0 | $10^2$ | $10^{2-3}$ | $10^{3-4}$ | $10^5$ |
| 96 | 0 | 0 | $10^{1-2}$ | $10^{1-2}$ | $10^2$ | $10^{2-3}$ | $10^{4-5}$ |
| 23 | 0 | 0 | 0 | $0-10^1$ | $10^{1-2}$ | $10^2$ | $10^{3-4}$ |

Non-treated = $10^5$

TABLE 19

EFFECTIVE VIRUCIDAL CONCENTRATION

| Compound | $IC_{50}$ |
|---|---|
| 93 | 0.5 mg/ml |
| 96 | 0.5–1.0 mg/ml |

TABLE 19-continued

EFFECTIVE VIRUCIDAL CONCENTRATION

| Compound | $IC_{50}$ |
|---|---|
| 23 | 0.1 mg/ml |

Comment:
Intracellular antiviral activity of the compounds is a minimum of one log higher than the virucidal activity.

EXAMPLE 2

A. VIRUS USED

VZV was grown to a CPE level in vitro assays with VZV of 3–4+ on HFF cell monolayers. The VZV was scraped from the flask, centrifuged and the cell pellet was resuspended in 10 ml of complete medium. One hundred to 200 µl of the VZV cell associated inoculum was inoculated onto confluent HFF cell monolayers by absorption for 60 minutes at 37° C. After absorption of the virus, the inoculum was aspirated from the cell monolayers.

B. PREPARATION OF SOLUTIONS TO BE TESTED

Concentrations of compounds 93, 96, and 23 were prepared as follows: A stock solution of each compound at a concentration of 5 mg/ml was made. This stock solution was serially diluted in Hanks Balanced Salt Solution to obtain final drug concentrations of: 5, 2, 1, 0.5, 0.1, 0.01, 0.001, and 0.0001 mg/ml. Five hundred µl of each drug concentration were added to triplicate infected monolayers. (Compound 93 was observed not to be soluble at 5 and 2 mg/ml concentrations. The highest concentration of this compound used in these assays was 1 mg/ml. As explained earlier, this was due to insufficient stirring.)

C. INOCULATION AND ANALYSIS

The VZV-infected monolayers were rehydrated with medium containing the appropriate concentrations of compounds to be tested. All monolayers were incubated at 37° C. Development of VZV cytopathology was monitored daily for 7 days by inverted light microscopy. Titers were calculated by multiple regression analysis.

CONTROLS

Sham-inoculated, non-treated HFF cell monolayers were included among with the drug-treated monolayers as cell monolayer controls.

VZV inoculated, non-treated HFF monolayers were included as positive controls.

RESULTS

Cell monolayer controls

No adverse HFF cellular effects were evident in these monolayers.

TABLE 20

VIRUCIDAL EFFICACY

7 Days Post Inoculation Efficacy: PFU/ml
Concentration (mg/ml)

| Compound | 5 | 2 | 1 | 0.5 | 0.1* | 0.01 | 0.001 |
|---|---|---|---|---|---|---|---|
| 93 | ND | ND | T | T | T? | $10^2$ | $10^4$ |
| 96 | 0 | 0 | T | T | T? | $10^2$ | $10^4$ |
| 23 | 0 | 0 | 0 | 0 | T? | $10^{1-2}$ | $10^{2-3}$ |

Non-treated = $10^4$
*This toxicity observation is questionable.

TABLE 21

EFFECTIVE VIRUCIDAL CONCENTRATION

| COMPOUND | $IC_{50}$ |
|---|---|
| 93 | 0.01 mg/ml |
| 96 | 0.01 mg/ml |
| 23 | 0.01–0.001 mg/ml |

IN VIVO STUDIES

The following examples describe topical ocular evaluation of the inventive compounds during RE strain HSV-1-induced stromal keratitis in the rabbit. These evaluations included analysis of the topical efficacy of both the inventive compounds alone, or, in certain instances, in combination with trifluorothymidine (TFT). The evaluation was carried out by the combined analysis of both clinical and virological (HSV-1 recovery) parameters.

Procedures common to each of the Examples are as follows:

Virus Inoculation

The specified number of NZW rabbits (1.5–2.0 kg) were used. Animals were received at least two days prior to inoculation to allow them to accommodate to the conditions in the vivarium facility. This conditioning of the animals prior to inoculation minimizes animal variability. After the accommodation, the animals received a slit-lamp examination to exclude any animals with pre-existing anterior segment ocular defects. Animals were bi-laterally inoculated by intrastromal injection of $10^5$ PFU RE strain HSV-1. The animals were then replaced individually into cages.

Animal Groupings and Daily Evaluations

On day number three post-inoculation (PI), the animals were evaluated by slit-lamp microscopy. Corneal stromal, iris and conjunctival disease were graded on an increasing scale of severity from 0+ to 4+. After evaluation, the animals were divided into a specified number of groups each containing an equal number of animals based on a matched corneal stromal involvement. Topical therapy was initiated immediately after animal groupings. All animals received daily slit-lamp evaluations from day 3 through 7 PI. The ocular HSV-1 induced disease severity was recorded daily.

HSV-1 Recovery from Conjunctival and Corneal Cultures

All eyes were monitored for the presence of infectious HSV-1 on day 0 (preculture), 3, 5 and 7 PI. This was carried out by obtaining tear film by swabbing the lower and upper conjunctival sacs and retaining the swab in the nasal fornix for 10 seconds. The swabs were eluted individually in HBSS. 50 μl aliquots of the virus-HBSS eluate were absorbed under confluent HFF cell monolayers for 5 minutes. The monolayers were hydrated with MEM, incubated at 37° C. and observed daily for 1 to 2 weeks to detect developing cytopathology consistent with HSV infection (HSV CPE). Cultures not exhibiting HSV CPE were blind passaged to confirm negativity.

Data Analysis

Clinical efficacy of the inventive compounds alone (or together with TFT in Example 4) was compared to the efficacy of TFT and placebo therapies. Differences in disease resolution and development of stromal alterations are statistically analyzed. Virus recovery during and after topical therapy was compared.

EXAMPLE 3

The topical efficacy of Compounds 23 and 96 on stromal HSV-1 infection in the rabbit model of stromal keratitis was evaluated.

A total of 20 NZW rabbits were used for this study. Therapy groups included:

Group #1: 5 rabbits, 1 mg/ml Compound 23 topical therapy 9×/day for 5 days;

Group #2: 5 rabbits, 1 mg/ml Compound 96 topical therapy, 9×/day for 5 days;

Group #3: 5 rabbits, 0.1% TFT topical therapy, 9×/day for 5 days;

Group #4: 5 rabbits, placebo (sterile water) therapy 9×/day for 5 days.

All animals received daily slit lamp evaluations from day 3 through day 7 and on days 9 and 10 PI. The ocular HSV-1-induced disease severity was recorded daily.

On day 10 PI, the animals were sacrificed, the corneal epithelium was scraped from the eyes and epithelial and corneal stromal cultures were preformed on HFF cell monolayers. The separation of epithelial virus from deeper stromal virus infection allows for analysis of HSV in these distinct corneal layers. Corneal epithelial and stromal co-cultures were evaluated daily by inverted light microscopy. Cultures not exhibiting HSV CPE were blind passaged to confirm negativity.

At sacrifice, trigeminal ganglia were removed, washed in HBSS, minced and floated over duplicate HFF cell monolayers. The cell co-cultures were monitored by inverted light microscopy for 2 weeks. Negative cultures were blind passaged twice at 7 day intervals. Detection of HSV CPE in the whole-cell co-cultures was scored either positive or negative. HSV recovery from inventive compound-treated, TFT-treated and placebo-treated trigeminal ganglia was compared and differences in recovery rates analyzed.

RESULTS

Four rabbits were sham inoculated and treated with compound 96 to evaluate potential ocular toxic effects on rabbit eyes at a 1 mg/ml therapy level. After topical therapy for 5 days, no toxic effects were evident and the cornea, conjunctiva and iris were clinically normal.

The efficacy of compounds 23 and 96 during HSV-1 stromal infection in the rabbit are shown in FIG. 1 along with TFT and placebo. All eyes in the therapy group were included in this analysis. As shown, therapy with compound 96 produce significantly better results than the other topical therapies on days 4, 5 and 6 PI (p<0.05). The efficacy ranking of the compounds testing during stromal HSV-1 infection of the rabbit is:

Compound 96>>Compound 23>TFT>Placebo.

The stromal disease development after inoculation was monitored in three different ways. FIG. 1 shows the first type of analysis in which all eyes were analyzed. In the second analysis, the therapy groups were divided into stromal disease classes of initial stromal disease severity <0.75 and >0.75 on the day therapy was initiated. The third analysis included comparison of the other ocular parameters of the HSV-1 infection. These parameters included epithelial HSV-1 lesions, conjunctivitis and iritis development in the rabbits.

Compound 96 demonstrated superior properties in all of the therapies used in the studies as compared to compound 23. In addition, compound 96 was superior to all other therapies in reducing and/or preventing the development of corneal stromal keratitis. Compound 23 was superior to TFT therapy on days 7, 9 and 10 PI. A lack of efficacy of topical therapy was observed when stromal disease involvement was at a moderate to high level (>0.75) on day 3 PI (the day the therapy was initiated.) However, topical therapy with compound 96 was statistically better than TFT, Placebo and Compound 23 on treated eyes with stromal disease development <0.75 on day 3 PI. The scarring demonstrated in the animals treated with compound 96 was significantly lower than the scarring in the TFT animals (scarring was clinically evident as stromal clouding and haze with or without neovascularization).

Table 22 below sets forth the results of virus recovery from tear film cultures on days 3, 5, 7 and 9 PI from corneal epithelium, corneal stroma, and trigeminal ganglia. The numbers in table one represent the percent of positive samples to the total number of samples. Tear film recovery of HSV-1 was significantly different in the TFT treated group on day 7 PI. However, the other differences shown between the compounds are not statistically significant However, the recovery of HSV-1 from the corneal epithelial cultures was significantly reduced for compound 23 treated eyes as compared to the other therapy groups. No significant differences were evident in HSV-1 recovery from the corneal stroma and from trigeminal ganglia cultures. This result is not unexpected because topically applied drugs either never reach the level of the trigeminal ganglion or reach the ganglion in concentrations below the minimal virustatic or virucidal levels.

TABLE 22

| Therapy group | Tear film (days post Inoculation) | | | | | | | |
|---|---|---|---|---|---|---|---|---|
| | 0 | 3 | 5 | 7 | 9 | C.E.* | C.S.* | T.G.* |
| Placebo | — | 100 | 100 | 90 | 0 | 90 | 60 | 70 |
| TFT | — | 100 | 80 | 30 | 0 | 60 | 60 | 60 |
| Compound 23 | — | 100 | 100 | 80 | 0 | 20 | 50 | 50 |
| Compound 96 | — | 100 | 100 | 80 | 0 | 50 | 50 | 50 |

*C.E. = Corneal Epithelium, C.S. = Corneal Stroma, T.G. = Trigeminal Ganglia

EXAMPLE 4

The topical efficacy of Compounds 23, 96 and 82 on stromal HSV-1 infection in the rabbit model of stromal keratitis was evaluated.

A total of 21 NZW rabbits were used for this study. Therapy groups included:

Group #1: 4 rabbits, 1 mg/ml Compound 23 topical therapy 9×/day for 5 days;

Group #2: 4 rabbits, 1 mg/ml Compound 96 topical therapy, 9×/day for 5 days;

Group #3: 5 rabbits, 1 mg/ml Compound 82 topical therapy, 9×/day for 5 days;

Group #4: 5 rabbits, 0.1% TFT topical therapy, 9×/day for 5 days;

Group #5: 4 rabbits, placebo therapy 9×/day for 5 days.

All animals received daily slit lamp evaluations for day 3 through day 7 PI. The ocular HSV-1-induced disease severity was recorded daily.

RESULTS

The stromal disease development after inoculation was monitored in three different ways. Firstly, the stromal disease scores for all eyes in a therapy group were analyzed. Secondly, the therapy groups were divided into stromal disease classes of initial stromal disease severity <0.5 and >0.5 on the day therapy was initiated. The third analyses included comparison of the other ocular parameters of the HSV-1 infection as in Example 3.

Compound 82 (1 mg/ml) was effective in reducing the development of stromal disease in eyes with stromal disease severity <0.5+ on day 3 PI. In eyes with stromal disease severity >0.75, Compound 82 therapy did not alter the development or progression of stromal disease. Compound 82 exhibited an efficacy intermediate between Compounds 23 and 96.

Compounds 23, 96 and 82 all reduced the recovery of HSV-1 in tear film. However, no statistically significant difference was evident between the inventive compounds and TFT.

FIG. 2 shows the average stromal disease scores or all compounds tested and indicates that the efficacy ranking of the compounds is:

Compound 96>Compound 82>Compound 23>TFT= Placebo

EXAMPLE 5

The topical efficacy of Compounds 23 and 96 in combination with TFT on stromal HSV-1 infection in the rabbit model of stromal keratitis was evaluated.

A total of 21 NZW rabbits were used for this study. Therapy groups included:

Group #1: 5 rabbits, Compound 23 (1 mg/ml) topical therapy, 4×/day plus TFT topical therapy, 4×/day for 5 days;

Group #2: 5 rabbits, Compound 96 (1 mg/ml) topical therapy, 4×/day plus TFT topical therapy, 4×/day for 5 days;

Group #3: 5 rabbits, placebo therapy, 8×/day for 5 days;

Group #4: 2 rabbits, 0.1% TFT topical therapy, 4×/day for 5 days;

Group #5: 2 rabbits, Compound 23 (1 mg/ml) topical therapy, 4×/day for 5 days;

Group #6: 2 rabbits, Compound 96 (1 mg/ml) topical therapy, 4×/day for 5 days.

Groups 1, 2 and 3 each have 5 animals for a total of 10 eyes per combination therapy. This allowed minimization of individual animal variability and performance of a statistical analysis on the results of the combination therapies. Groups 3, 4 and 5 have 2 animals each. These single-agent therapies were used to verify previously reported data on the efficacy of these compounds. The compounds are used at a lower frequency of delivery to match the dosing regimen of the combination-agent group. Consequently, the study also provides comparative information on Compounds 23 and 96 as a lower frequency of topical administration (4 times per day vs. 9 times per day in previous studies).

On day 7 PI, the animals were sacrificed, the corneal epithelium was scraped from the eyes and epithelial and corneal stromal cultures were performed on HFF cell monolayers. The separation of epithelial virus from deeper stromal virus infection allows for analysis of HSV in these distinct corneal layers. Corneal epithelial and stromal co-cultures were evaluated daily by inverted light microscopy. Cultures not exhibiting HSV CPE were blind passaged to confirm negativity.

RESULTS

FIG. 3 shows the combination drug therapeutic efficacy on stromal disease when the average stromal disease score was <0.5 on day 3 PI. Combination therapy with either Compound 23 or Compound 96 was effective in reducing the development of stromal disease in the rabbit cornea. The combination therapy for eyes stromal disease scores were statistically different from placebo therapy on days 6 and 7 PI (p<0.01: Student's T test). No statistical difference between Compound 96 and Compound 23 combination therapies was observed during the course of this study.

FIG. 4 shows the combination drug therapeutic efficacy on stromal disease when the average stromal disease core was >0.5 on day 3 PI. Stromal disease was unresponsive to the topical combination therapy in these moderate to severe stromal disease eyes.

FIG. 5 shows the efficacy of single-agent TFT, compound 23 and Placebo therapy as compared to combination TFT plus Compound 23 when the initial stromal disease was <0.5 on day 3 PI. TFT and Placebo therapies were ineffective in reducing the stromal disease severity. Compound 23 slowed the progression of stromal disease. The combination drug therapy was effective in reducing the progression of stromal disease in these animals. The combination therapy results were statistically difference from all other therapies on day 7 PI.

FIG. 6 discloses the efficacy of a single-agent TFT, Compound 20 or Compound 23 vs. Placebo therapy and vs. a combination TFT plus Compound 23 therapy when initial stromal disease was >0.5 on day 3 PI. No single-agent or combination agent therapy appear to be effective in reducing the progression of stromal disease in these eyes.

FIG. 7 compares the combination drug therapeutic efficacy vs. the single-agent therapy on stromal disease when the average stromal disease score was <0.5 on day 3 PI. Placebo and TFT therapies (4 times per day) were ineffective in reducing the development and progression of stromal disease. Therapy with the Compound 96 at a frequency of 4 times per day was highly effective and slowed the progression and development stromal disease. Average stromal disease for this treatment group was statistically different from both the Placebo and TFT therapies and days 6 and 7 PI (p<0.01). No difference was seen between Compound 96 as a single-agent and Compound 96 plus TFT as a combination agent. The combination drug therapy was also highly effective in reducing stromal disease. The combination therapy group was statistically difference from the TFT and Placebo therapy groups on days 6 and 7 PI (p<0.01). No statistical difference in stromal disease scores was observed between Compound 96 as a single-agent and the combination of Compound 96 with TFT.

FIG. 7 shows the comparison of the combination drug therapeutic efficacy with single-agent therapy on HSV induced stromal disease when the average disease score was >0.5 on day 3 PI. Neither the combination nor single-agent therapy has any effect on reducing the development and progression of the disease.

Table 23 shows the HSV-1 recovery from single-agent and combination-agent ocular therapies. The numbers represent the % positive recovery cultures per total number of cultures.

TABLE 23

| Therapy Group | 1 | 3 | 5 | 7 | Corneal Stroma |
|---|---|---|---|---|---|
| Compound 96 (single-agent) | 0 | 100 | 90 | 70 | 70 |
| Compound 23 (single-agent) | 0 | 100 | 90 | 80 | 80 |

TABLE 23-continued

| Therapy Group | 1 | 3 | 5 | 7 | Corneal Stroma |
|---|---|---|---|---|---|
| TFT (single-agent) | 0 | 100 | 90 | 70 | 70 |
| Compound 23 + TFT | 0 | 100 | 80 | 60 | 70 |
| Compound 96 + TFT | 0 | 100 | 80 | 50 | 50 |
| Placebo | 0 | 100 | 100 | 90 | 90 |

*The reduction in tear film virus recovery in the Compound 96 + TFT therapy eyes appears to be an additive effect, as the recovery of virus from the tear film and from the corneal stroma cultures in combination-treated eyes were reduced compared to single-agent Compound 96 or TFT therapy.

As shown in Table 23, the recovery of virus in the combination therapy eyes was lower than the single-agent treated eyes.

EXAMPLE 6

A series of studies were carried out to compare the activity of inventive antiviral Compounds 23, 76, and 82 in a primary genital HSV-2 infection of guinea pigs. The experiments were placebo-controlled and uninfected animals were treated with three concentrations of each of the preparations to assess skin irritation and determine the maximum tolerated dose.

General HSV-2 Infection of Guinea Pigs
A. Determination of Maximum Tolerated Dose Groups of three uninfected animals were treated topically (0.1 ml intravaginally +0.1 ml on the external genital skin) three times daily (approximately every eight hours) for seven days with concentrations of 20, 10 or 5 mg/ml of each compound to assess any skin irritation or visible toxicity.

B. Virus and Viral Inoculation

The MS strain of HSV-2 was utilized for the experimental animal infection. Female Hartley strain guinea pigs (Charles River Breeding Laboratories, Kingston, N.Y.) weighing 250–300 g were inoculated intravaginally with $1.4 \times 10^5$ plaque forming units of HSV-2 one hour after being swabbed for the removal of vaginal secretions.

C. Treatment of Guinea Pigs

Groups of 10 infected guinea pigs were treated topically as stated above with 20 mg/ml (the maximum tolerated dose) of each compound beginning 6 h or 24 h after inoculation with HSV-2.

D. Sample Collection and Virus Assays

To determine the effect of treatment on vaginal virus replication, swabs of vaginal secretions were obtained on days 1, 3, 5, 7, and 10 after HSV-2 inoculation, placed in a tube containing 2.0 ml of media, vortexed and frozen at −70° until titrated for HSV-2. When all samples were collected, they were thawed, diluted serially and HSV-2 titers were determined using rabbit kidney cells in a microtiter CPE assay. Mean peak virus titers and areas under the virus titer-day curves were calculated and analyzed.

E. Scoring of External Genital Lesions

To determine the effect of therapy on the development and spread of external genital lesions, lesion severity was scored on a 0–5+ scale through the primary infection (21 days). Mean peak lesion scores and the areas under the lesion score-day curves were calculated and analyzed.

F. Evaluation of Efficacy

The number of animals infected over the number inoculated, lesion score-day areas and virus titer-day areas under the curve, peak lesion scores and peak virus titers between untreated and placebo-treated or placebo-treated and drug-treated animals were compared using the Mann- Whitney U rank sum test. A p-value of 0.05 or less was considered significant.

RESULTS

Effect of Treatment with Compound 23, Compound 76 or Compound 82 on Skin Irritation Groups of 3 guinea pigs were treated with 20, 10 or 5 mg/ml of Compound 23, Compound 76 or Compound 82 as described previously. No visible signs of any skin irritation or genital toxicity with the three compounds at these concentrations were observed. The animals remained healthy and normal in appearance throughout the study.

II. Effect of Treatment with Compound 23, Compound 76 or Compound 82 on Vaginal Virus Replication After HSV-2 inoculation, viral replication in the vaginal tract reaches a peak on days 3–5, then declines gradually with most animals having cleared the virus by day 10. Evaluation of therapy with topical Compound 23, Compound 76, and Compound 82 on vaginal virus titers is summarized in Table 24. Early treatment with all three compounds reduced the number of animals that became infected with HSV-2 (had virus isolated on at least one swab day). Animals that received Compound 23, Compound 76 or Compound 82 beginning 6 h after infection had an infectivity rate of 50%. In all other groups, all animals (100%) inoculated became infected.

The animals treated with placebo initiated 6 h or 24 h after viral inoculation had virus titer-day areas under the curve (AUC) values and mean peak virus titers that were similar to the untreated control group. The virus titer-day AUC values in animals that received the Compound 23, Compound 76 or Compound 82 beginning 6 h post-inoculation were reduced significantly when compared to the placebo-treated group (P-values of <0.001). Treatment with these compounds at +6 h also significantly decreased the mean peak virus titers compared with the placebo-treated animals (P-values of <0.001). Therapy with Compound 23 or Compound 76 beginning 24 h after viral inoculation also reduced the virus titer AUC (P-values of <0.05). Treatment with Compound 82 at +24 h failed to alter the virus titer AUC and none of the compounds reduced the mean peak virus titer when given at +24 h.

III. Effect of Treatment with Compound 23, Compound 76 or Compound 82 on Lesion Development Three to four days after HSV-2 inoculation, vesicular lesions begin to appear on the external genital skin. Lesions progress to an ulcerative stage by days 7–8 and gradually heal by days 15–21. Evaluation of topical Compound 23, Compound 76, and Compound 82 therapy on lesion development and severity is shown in Table 25. The animals treated with the placebo at +6 h and +24 h had significantly increased lesion score-day AUC values when compared to the untreated control group (P-values of <0.001). The mean peak lesion score for the placebo given at +6 h was also significantly greater than those of the untreated control animals (P-value of <0.05). Lesion development as determined by both lesion score-day AUC values and mean peak lesion scores was significantly reduced by treatment with Compound 23, Compound 76 or Compound 82 when initiated 6 h after infection when compared to the appropriate placebo-treated animals (P-values of <0.001). Also, Compound 76 administered +24 h of infection significantly altered the lesion AUC (P-value of <0.01), but only when compared to the +24 h placebo-treated group. This difference was not significant when compared to the untreated control animals.

TABLE 24

EVALUATION OF TOPICAL COMPOUND 23, COMPOUND 76, AND COMPOUND 82 THERAPY ON INFECTION RATES AND VAGINAL VIRUS TITERS DURING A PRIMARY GENITAL HSV-2 INFECTION OF GUINEA PIGS

| Compound[a] | # Infected/ # Inoculated | Virus Titer-Day Area Under Curve | P-Value | Mean Peak Virus Titer | P-Value |
|---|---|---|---|---|---|
| Control | 10/10 | 28.8 | — | 4.6 | — |
| Placebo +6h | 10/10 | 29.1 | NS[b] | 4.6 | NS |
| 23 +6h | 5/10 | 1.7 | <0.001 | 1.1 | <0.001 |
| 76 +6h | 5/10 | 2.9 | <0.001 | 1.0 | <0.001 |
| 82 +6h | 5/10 | 3.3 | <0.001 | 1.1 | <0.001 |
| Placebo +24h | 10/10 | 28.5 | NS | 4.5 | NS |
| 23 +24h | 10/10 | 14.5 | <0.05 | 4.1 | NS |
| 76 +24h | 10/10 | 17.7 | <0.05 | 4.3 | NS |
| 82 +24h | 10/10 | 26.4 | NS | 4.6 | NS |

[a] Treatment with 20 mg/ml was initiated at the times indicated and was continued three times daily for seven days both topically and intravaginally.
[b] NS = Not Statistically Significant when compared to the untreated control or appropriate placebo-treated group.

TABLE 25

EVALUATION OF TOPICAL COMPOUND 23, COMPOUND 76 AND COMPOUND 82 THERAPY ON LESION DEVELOPMENT DURING A PRIMARY GENITAL HSV-2 INFECTION OF GUINEA PIGS

| Compound | Lesion Score-Day Area Under Curve | P-Value | Mean Peak Lesion Score | P-Value |
|---|---|---|---|---|
| Control | 31.4 | — | 2.6 | — |
| Placebo +6h | 48.6 | 0.001 | 3.8 | <0.05 |
| 23 +6h | 0.0 | <0.001 | 0.0 | <0.001 |
| 76 +6h | 4.4 | <0.001 | 0.4 | <0.001 |
| 82 +6h | 3.5 | <0.001 | 0.7 | <0.001 |
| Placebo +24h | 46.7 | <0.001 | 3.6 | NS[b] |
| 23 +24h | 43.8 | NS | 3.4 | NS |
| 76 +24h | 37.2 | <0.01 | 3.3 | NS |
| 82 +24h | 53.8 | NS | 3.4 | NS |

*Treatment with 20 mg/ml was initiated at the times indicated and was continued three times daily for seven days both topically and intravaginally.

EXAMPLE 7

A series of viral screening tests were carried out for Compounds 23, 64, 67, 93, 96, and 102. The structure of Compounds number 64 and 67 are set forth in U.S. Pat. No. 5,049,557 at paragraphs 2 and 3 of the Experiment Details section. In particular, for Compound 64, A is phenyl, Y is hydrogen, B is methyl, Z– is chloride, and X and X' are $NH_3$. For Compound 67, A is methyl, B is methyl, Y is chlorine, Z– is chloride and X and X' are $NH_3$. Compounds 23, 64 and 67 were screened for comparison purposes. The results are shown in Table 26.

The following procedures were utilized for determining antiviral efficacy and toxicity:

A. Preparation of Human Foreskin Fibroblast Cells

Newborn human foreskins were obtained as soon as possible after circumcisions were performed and placed in minimal essential medium (MEM) containing vancomycin, fungizone, penicillin, and gentamycin, at the usual concentrations, for four hours. The medium was then removed, the foreskin minced into small pieces and washed repeatedly until red cells were no longer present. The tissue was then trypsinized using trypsin at 0.25% with continuous stirring for 15 minutes at 37° C. in a $CO_2$ incubator. At the end of each 15 minute period the tissue was allowed to settle to the bottom of the flask. The supernatant containing cells was poured through sterile cheesecloth into a flask containing MEM and 10% fetal bovine serum. The flask containing the medium was kept on ice throughout the trypsinizing procedure. After each addition of cells, the cheese cloth was washed with a small amount of MEM containing serum. Fresh trypsin was added each time to the foreskin pieces and the procedure repeated until no more cells became available. The cell containing medium was then centrifuged at 1000 RPM at 4° C. for ten minutes. The supernatant liquid was discarded and the cells resuspended in a small amount of MEM with 10% FBS. The cells were then placed in an appropriate number of 25 $cm^2$ tissue culture flasks. As cells became confluent and needed trypsinization, they were gradually expanded into larger flasks. The cells were kept on vancomycin and fungizone to passage four.

B. Cytopathic Effect Inhibition Assay

Low passage human foreskin fibroblast cells were seeded into 96 well tissue culture plates 24 hours prior to use at a cell concentration of $2.5 \times 10^4$ cells per ml in 0.1 ml (MEM) supplemented with 10% fetal bovine serum (FBS). The cells were then incubated for 24 hour at 37° C. in a $CO_2$ incubator. After incubation, the medium was removed and 100 µl of MEM containing 2% FBS was added to all but the first row. In the first row, 125 µl of experimental drug was added in triplicate wells. Medium alone was added to both cell and virus control wells. The drug in the first row of wells was then diluted serially 1:5 throughout the remaining wells by transferring 25 µl using the Cetus Liquid Handling Machine. After dilution of drug, 100 µl of the appropriate virus concentration was added to each well, excluding cell control wells which received 100 µl of MEM. For HSV-1 and HSV-2 assays, the virus concentration utilized was 1000 PFU's per well. For CMV and VZV assays, the virus concentration added was 2500 PFU per well. The plates were then incubated at 37° C. in a $CO_2$ incubator for three days for HSV-1 and HSV-2, 10 days for VZV, or 14 days for CMV. After the incubation period, media was aspirated and the cells stained with a 0.1% crystal violet solution for 30 minutes. The stain was then removed and the plates rinsed using tap water until all excess stain was removed. The plates were allowed to dry for 24 h and then read on a Skatron Plate Reader at 620 nm.

C. Plaque Reduction Assay for HSV-1 and HSV-2 Using Semi-Solid Overlay

Two days prior to use, HFF cells are plated into six well plates and incubated at 37° C. with 5% $CO_2$ and 90% humidity. On the date of assay, the drug is made up at twice the desired concentration in 2×MEM and then serially diluted 1:5 in 2×MEM using six concentrations of drug. The initial starting concentration is usually 200 µg/ml down to 0.06 µg/ml. The virus to be used is diluted in MEM containing 10% FBS to a desired concentration which will give 20–30 plaques per well. The media is then aspirated from the wells and 0.2 ml of virus is added to each well in duplicate with 0.2 ml of media being added to drug toxicity wells. The plates are then incubated for one hour with shaking every fifteen minutes. After the incubation period, an equal amount of 1% agarose was added to a equal volume of each drug dilution. This will give final drug concentrations beginning with 100 µg/ml and ending with 0.03 µg/ml and a final agarose overlay concentration of 0.5%. The drug agarose mixture is applied to each well in 2 ml volume and the plates then incubated for three days, after which the cells were stained with a 1.5% solution of neutral red. At the end of 4–6 hr incubation period, the stain is aspirated, and plaques counted using a stereomicroscope at 1×magnification.

D. VZV Plaque Reduction Assay—Semi-Solid Overlay

The procedure is essentially the same as for the HSV plaque assay described above with two exceptions:

1. After addition of the drug, the plates are incubated for ten days.
2. On days three and six an additional 1 ml overlay with equal amounts of 2×MEM and 1% agarose are added.

E. CMV Plague Assay—Semi-Solid Overlay

The procedure is essentially the same as for HSV analysis with the following minor changes. The agarose used for the initial overlay and the two subsequent overlays is 0.8% rather than 1%. The assay is incubated for 14 days with the additional 1 ml overlays being applied on days four and eight.

F. Plaque Reduction Assays Using Liquid Medium Overlay

The procedure for the liquid overlay plaque assay is similar to that using the agarose overlay. The procedure for adding the virus is the same as for the regular plaque assay. The drugs are made up in a concentration to be used in MEM with 2% FBS. The drugs are not made up at 2×concentration as in previous assays but are made up at the desired concentration. For HSV-1 and HSV-2 assays, an antibody preparation obtained from Baxter Health Care Corporation is diluted 1:500 and added to the media that the drug is diluted in. For CMV and VZV, no antibody in the overlay is utilized. For the CMV assay, additional medium without new drug is added on day six and allowed to incubate for a total of 11 days. For VZV, additional media is added on day five and incubated for a total of eight days. At the end of the incubation period for all of the assays, the medium is removed, the cells washed and then stained with 0.1% crystal violet solution for ten minutes. The cells are then rinsed several times to remove any excess crystal violet and plaques enumerated using a stereomicroscope.

G. Cell Proliferation Assay

Twenty-four hours prior to assay, HFF cells are seeded in 6-well plates at a concentration of $2.5 \times 10^4$ cells per well in MEM containing 10% FBS. On the day of the assay, drugs are diluted serially in MEM containing 10% FBS at increments of 1:5 covering a range from 100 µg/ml to 0.03 µg/ml. For drugs that have to be solubilized in DMSO, control wells receive MEM containing 10% DMSO. The media from the wells is then aspirated and 2 ml of each drug concentration is then added to each well. The cells are then incubated in a $Co_2$ incubator at 37° C. for 72 h. At the end of this time, the media-drug solution is removed and the cells washed. One ml of 0.25% trypsin is added to each well and incubated until the cells start to come off of the plate. The cell-media mixture is then pipetted up and down vigorously to break up the cell suspension and 0.2 ml of the mixture is added to 9.8 ml of Isoton III and counted using a Coulter Counter. Each sample is counted three times with three replicate wells per sample.

H. MTT Assay For Cell Cytotoxicity

Twenty-four hours prior to assay, HFF cells are plated into 96 well plates at a concentration of $2.5 \times^4$ cells per well. After 24 h, the media is aspirated and 1256 microliters of drug is added to the first row of wells and then diluted serially 1:5 using the automated Cetus Liquid Handling System in a manner similar to that used in the CPE assay. The plates are then incubated in a $CO_2$ incubator at 37° C. for seven days. At this time, each well receives 50 microliters of 1 µg/ml solution of MTT in Dulbecco's Phosphate Buffered Saline. The plates are then incubated for an additional four hours. At this time, the media is removed and replaced with 100 μl of 0.04N hydrochloric acid in isopropanol. After shaking briefly, the plates are then read on a plate reader at 550 nm.

I. EC50 values were also determined for each of the viruses tested for known antiviral agents. The comparison compound was ACV for all viruses except for HCMV aherein DHPG was the comparison compound. In Table 26, these comparison EC50 values are indicated with an asterisk. In Table 27, the drug FIAU (2'-fluoro-5-iodo-arabinosyl-uracil) was used as a control.

by mixing equimolar amounts of the N,N'-bisethylenediimine ligands, e.g., L23 and the like as disclosed in U.S. Pat. No. 5,049,557 with cobalt acetate in methanol under nitrogen. About 2.2 equivalents of the desired axial ligand is added followed by oxidation. The desired product may then be precipitated by the addition of a saturated aqueous solution of sodium chloride or sodium bromide followed by recrystallization from an ethanol-water solution.

Compound 96 (having bromide as the counterion) was synthesized as follows:

TABLE 26

ANTIVIRAL ACTIVITY

| COMPOUND | | HSV-1 | | HSV-2 | | HCMV | | V2V | | EBV |
|---|---|---|---|---|---|---|---|---|---|---|
| | | CPE | PLAQUE | CPE | PLAQUE | CPE | PLAQUE | CPE | PLAQUE | IMN |
| 23 | EC50 | 16.5 | >4 | 4.6 | >4 | 14.6 | 15.6 | | >4 | 2.7 |
| | IC50 | >86 | 7.0 | >86 | 7.0 | >97 | 26.2 | | 11 | 1.9 |
| | SI | >5.2 | <1.7 | >19 | <1.7 | >6.6 | 1.7 | | <2.7 | 0 |
| | EC50 | .20 | .2 | .70 | .9 | .1 | .9 | | 3.2 | 5.8 |
| 64 | EC50 | 10.3 | | 6.2 | | 52.4 | >4 | | >4 | 2.7 |
| | IC50 | >87 | | >87 | | >73 | 9.9 | | 18 | 4.5 |
| | SI | >8.4 | | >14 | | >1.4 | 2.5 | | <4.5 | 1.7 |
| | EC50 | .20 | | .70 | | .10 | 0.7 | | 3.2 | 6.0 |
| 67 | EC50 | 3.2 | | 1.7 | | >100 | | | >2 | 0.6 |
| | IC50 | >100 | | >100 | | >79 | | | 11.5 | 3.6 |
| | SI | >31 | | >60 | | 0 | | | <5.7 | 6.0 |
| | EC50 | .20 | | .70 | | 0.8 | | | 4.4 | 3.6 |
| 93 | EC50 | 29.0 | | 6.1 | | >52 | 44.7 | | >3.3 | 2.7 |
| | IC50 | >94 | | >94 | | >100 | 41.4 | | 8.2 | 2.4 |
| | SI | >3.2 | | >15 | | <1.9 | 0 | | <2.5 | 0 |
| | EC50 | .20 | | .70 | | 0.8 | 0.73 | | 3.1 | 3.6 |
| 96 | EC50 | 6.8 | >4 | 5.3 | >4 | 17.5 | | | >4 | 1.3 |
| | IC50 | 80.0 | 10.2 | 80.0 | 10.2 | >83 | | | 26 | 7.3 |
| | SI | 12 | <2.5 | 15 | <2.5 | >4.7 | | | <6.5 | 5.6 |
| | EC50 | 0.20 | 0.2 | 0.70 | 0.9 | 0.8 | | | 3.0 | 3.6 |
| 102 | EC50 | 1.7 | 5.6 | 5.0 | 2.2 | 33 | | | >12 | 0.67 |
| | IC50 | >92 | 11.5 | >92 | 11.5 | >100 | | | 27 | 2.2 |
| | SI | >54 | 2.0 | >18 | 5.2 | >3.3 | | | <2.2 | 3.3 |
| | EC50 | 0.20 | 0.2 | 0.70 | 0.3 | 0.05 | | | 3.0 | 3.6 |

TABLE 27

TOXICITY ASSAYS-IC$_{50}$

| COMPOUND | NEUTRAL RED UPTAKE (MCG/ML) (STATIONARY CELLS) | MTT TOXICITY (MCG/ML) (STATIONARY CELLS) | CELL PROLIFERATION (MCG/ML) (RAPIDLY GROWING CELLS) |
|---|---|---|---|
| 23 | 11.5 | >61 | 6.2 |
| FIAU | — | — | 13.1 |
| 64 | 15.2 | 53 | 38 |
| FIAU | — | — | 8.4 |
| 67 | 12.1 | 42.0 | 12.0 |
| FIAU | — | — | 8.4 |
| 93 | 27.3 | 65.0 | 25.0 |
| FIAU | — | — | 8.4 |
| 96 | 22.0 | >74 | 21.0 |
| FIAU | — | — | 3.3 |
| 102 | 23.2 | >68 | 15 |
| FIAU | — | — | 3.3 |

EXAMPLE 8

The compounds of the present invention may be prepared by the following general procedure. The cobalt-II prepared A 3-necked flask equipped with a nitrogen bubbler and a 2 liter dropping funnel was charged with 112 grams (0.5 moles) of the ligand (L23 or N,N'bis-(acetylacetone) ethylenediimine) in 500 ml of absolute methanol. To the ligand solution is added 125 grams (0.5 moles) of cobalt acetate tetrahydrate dissolved in 1.5 liters of degassed methanol. The reaction mixture is stirred for 2 hours and then refluxed for 15 minutes on a hot water bath. An orange solution results to which 90 grams (1.1 moles) of 2-methyl imidazole dissolved in 100 ml of methanol are added. The reaction mixture is exposed to the open air while maintaining vigorous stirring. Ten grams of activated charcoal are added to the stirring mixture and the oxidation is continued overnight.

The mixture is then filtered and 50 grams of sodium bromide dissolved in a minimum amount of water is added to the filtered brown solution. The solution obtained and is concentrated and allowed to crystallize. The crude product is recrystallized from hot ethanol-water solution by standing at room temperature or a lower temperature. The purity of the product is checked by elemental analysis, electronic spectra and NMR.

What is claimed is:

1. A compound having the structure

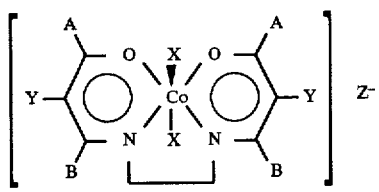

wherein each

A may be the same or different and is an alkyl group, a phenyl group or a substituted derivative of a phenyl group;

Y may be the same or different and is hydrogen, an unbranched alkyl group, a halide or a group having the structure

wherein R is hydrogen, an alkoxide group, an alkyl group, or OH;

B may be the same or different and each is hydrogen or an alkyl group;

$Z^-$ is a soluble, pharmaceutically acceptable negative ion, and

X may be the same or different and is an axial ligand selected from the group consisting of moieties having the formula:

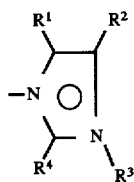

wherein $R^1$, $R^2$, $R^3$, and $R^4$ may be the same or different and may be hydrogen or lower alkyl having from 1 to 4 carbon atoms;

with the proviso that $R^1$, $R^2$, $R^3$, and $R^4$ are of a sufficiently small size so as not to prohibit the attachment of the axial ligand to the Co atom due to steric hindrance.

2. The compound of claim 1 wherein A is a $C_1$–$C_5$ alkyl group, a phenyl group or a substituted phenyl group having substituents selected from the group consisting of halide, alkyl or a group having the structure

where R is hydrogen, an alkoxide group, an alkyl group or OH; Y is hydrogen or an unbranched alkyl group, halide, or a group having the structure

wherein R is H, $CH_3$, or OH; B is hydrogen or a $C_1$–$C_3$ alkyl group; and $Z^-$ is $Br^-$ or $Cl^-$.

3. The compound of claim 1 wherein A is methyl, ethyl, butyl, or phenyl; Y is chlorine, hydrogen or a $C_1$–$C_3$ alkyl group; and B is $C_1$–$C_3$ alkyl.

4. The compound of claim 1 wherein B is methyl, Y is H, or Cl; $Z^-$ is $Cl^-$ or $Br^-$; A is —$CH_3$ or phenyl and X is selected from the group consisting of

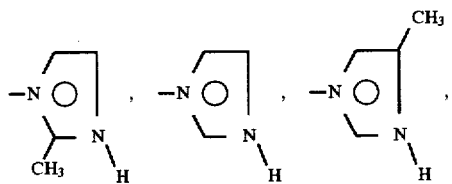

and

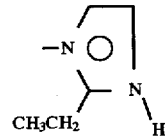

5. An antiviral composition comprising a pharmaceutically acceptable carrier and an antivirally effective amount of the compound of claim 1.

6. An antiviral composition comprising a pharmaceutically acceptable carrier and an antivirally effective amount of the compound of claim 2.

7. An antiviral composition comprising a pharmaceutically acceptable carrier and an antivirally effective amount of the compound of claim 3.

8. An antiviral composition comprising a pharmaceutically acceptable carrier and an antivirally effective amount of the compound of claim 4.

9. The composition of claim 5 wherein the compound is present in an antiherpes effective amount.

10. The composition of claim 5 wherein the compound is present in an effective amount against a virus selected from the group consisting of herpes simplex virus, cytomegalovirus, varicella-zoster virus, and Epstein-Barr virus.

11. In a method for treating a subject having a disease caused by a virus wherein a compound is administered to the subject in an antivirally effective amount, the improvement which comprises said compound being the compound claim 1.

12. In a method for treating a subject having a disease caused by a virus wherein a compound is administered to the subject in an antivirally effective amount, the improvement which comprises said compound being the compound claim 2.

13. In a method for treating a subject having a disease caused by a virus wherein a compound is administered to the subject in an antivirally effective amount, the improvement which comprises said compound being the compound claim 3.

14. In a method for treating a subject having a disease caused by a virus wherein a compound is administered to the subject in an antivirally effective amount, the improvement which comprises said compound being the compound claim 4.

15. In a method for treating a subject having a disease caused by a virus wherein a composition containing a pharmaceutically acceptable carrier and a compound which is administered to the subject in an antivirally effective amount, the improvement which comprises said composition being the composition of claim 5.

16. In a method for treating a subject having a disease caused by a virus wherein a composition containing a pharmaceutically acceptable carrier and a compound which is administered to the subject in an antivirally effective amount, the improvement which comprises said composition being the composition of claim 6.

17. In a method for treating a subject having a disease caused by a virus wherein a composition containing a pharmaceutically acceptable carrier and a compound which is administered to the subject in an antivirally effective amount, the improvement which comprises said composition being the composition of claim 7.

18. In a method for treating a subject having a disease caused by a virus wherein a composition containing a pharmaceutically acceptable carrier and a compound which is administered to the subject in an antivirally effective amount, the improvement which comprises said composition being the composition of claim 8.

19. The method of claim 15 wherein the virus is a herpes virus and the composition is administered in an anti-herpes effective amount.

* * * * *